(12) United States Patent
Schildbach et al.

(10) Patent No.: US 8,748,645 B2
(45) Date of Patent: Jun. 10, 2014

(54) WATER-SOLUBLE ORGANOSILICONATE POWDER

(75) Inventors: Daniel Schildbach, Altoetting (DE); Dominik Auer, Altoetting (DE); Karl-Heinz Felix, Reut (DE); Michael Stepp, Ueberackern Oesterreich (AT)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/810,676

(22) PCT Filed: Jul. 11, 2011

(86) PCT No.: PCT/EP2011/061766
§ 371 (c)(1),
(2), (4) Date: Jan. 25, 2013

(87) PCT Pub. No.: WO2012/022544
PCT Pub. Date: Feb. 23, 2012

(65) Prior Publication Data
US 2013/0145966 A1    Jun. 13, 2013

(30) Foreign Application Priority Data
Jul. 21, 2010 (DE) .......................... 10 2010 031 624

(51) Int. Cl.
*C07F 7/02* (2006.01)
(52) U.S. Cl.
USPC ........................................ 556/400

(58) Field of Classification Search
USPC ................................. 556/400, 465
See application file for complete search history.

(56) References Cited

U.S. PATENT DOCUMENTS

| | | | | |
|---|---|---|---|---|
| 2,438,055 A | * | 3/1948 | Hyde | 556/459 |
| 2,567,110 A | | 9/1951 | Hyde | |
| 2,803,561 A | * | 8/1957 | Kather | 427/243 |
| 4,252,569 A | * | 2/1981 | Roedel | 106/287.16 |
| 5,401,432 A | | 3/1995 | Jourbert et al. | |
| 6,268,423 B1 | | 7/2001 | Mayer et al. | |
| 6,368,659 B1 | | 4/2002 | Weber et al. | |

FOREIGN PATENT DOCUMENTS

| | | |
|---|---|---|
| DE | 1176137 B | 8/1964 |
| DE | 4336600 C1 | 10/1994 |
| EP | 0992565 A1 | 4/2000 |
| JP | 2003188196 A | 8/1991 |
| JP | 2011310706 A | 11/1991 |
| JP | 2008223156 A | 9/2008 |
| WO | 2010052201 A1 | 5/2010 |

* cited by examiner

*Primary Examiner* — Porfirio Nazario Gonzalez
*Assistant Examiner* — Kofi Adzamli
(74) *Attorney, Agent, or Firm* — Brooks Kushman P.C.

(57) ABSTRACT

Organosilanolate powders having a low cation to silicon ratio provide superior hydrophobing ability. The powders may be prepared on an industrial scale by hydrolysis of a silane with a basic salt solution, adding an inert organic solvent, and removing gaseous or alcoholic hydrolysis products by evaporation or distillation, precipitating the organosilanolate as a fine powder.

22 Claims, No Drawings

WATER-SOLUBLE ORGANOSILICONATE POWDER

CROSS-REFERENCE TO RELATED APPLICATIONS

This application is the U.S. national phase of PCT Appln. No. PCT/EP2011/061766 filed Jul. 11, 2011, which claims priority to German Patent Application No. 10 2010 031 624.5 filed Jul. 21, 2010, which are incorporated herein by reference.

BACKGROUND OF THE INVENTION

1. Field of the Invention

The invention relates to water-soluble organosiliconate powders, to a process for producing them, and to their use, especially for hydrophobizing mineral building materials.

2. Description of the Related Art

Alkali metal organosiliconates such as potassium methylsiliconate have already been used for decades to make materials hydrophobic, especially mineral building materials. On account of their high solubility in water, they can be applied in the form of an aqueous solution to solids, where evaporation of the water is accompanied by the formation of durably water-repellent surfaces which adhere firmly under the influence of carbon dioxide. Since they contain virtually no hydrolytically eliminable organic radicals, curing takes place, advantageously, without release of unwanted volatile organic by-products.

The preparation of alkali metal organosiliconates, especially potassium or sodium methylsiliconates, has been often described. In the majority of cases, the focus is on producing aqueous solutions which are ready for application and are stable in storage.

For example, DE 4336600 claims a continuous process starting from organotrichlorosilanes and proceeding via the corresponding organotrialkoxysilanes as intermediates. Advantageous features of this process are that the alcohol and hydrogen chloride by-products formed are recovered and that the siliconate solution formed is virtually chlorine-free. As a precondition for miscibility with water and for storage stability of the solutions, a molar ratio of alkali metal hydroxide to alkoxysilane of at least 1 is described.

This is also confirmed in other patents, as for example in U.S. Pat. No. 4,252,569, where for the preparation of aqueous alkali metal siliconate solutions a molar ratio of alkali metal hydroxide to chlorosilane (the hydrolysis/alkoxylation product thereof is used) of at least 0.9 to 1 is specified as a precondition for a complete reaction and for solubility of the resultant alkali metal siliconate.

A disadvantage of these products is that the active ingredient content—corresponding to the silicone fraction—is coupled with a minority of alkali metal. Reducing the molar ratio of alkali metal to silicon to levels significantly <1, while retaining efficacy, would be an economic and technical advantage.

Water-soluble organosiliconates are especially suitable for hydrophobizing—that is, for imparting water repellency to—building materials. Generally speaking, these are inorganic building materials, which may be silicatic or nonsilicatic in nature. The aqueous solution of methylsiliconate, in particular, is of great significance. This is more particularly true of the potassium derivative (potassium methylsiliconate) or the sodium derivative (sodium methylsiliconate).

Aqueous solutions of organosiliconates are especially suitable for hydrophobizing weakly acidic to weakly alkaline building materials, more particularly products comprising fired clay, natural stone or gypsum. The hydrophobizing agent may be applied either by impregnation or mass hydrophobizing. In the case of impregnation, for example, products of fired clay or natural stone are immersed for a certain time into an aqueous dilution of the organosiliconate or are sprayed with a dilution of this kind, the active substance in solution in water penetrating the porous microstructure of the building material by capillary action. After a time of a few minutes or several hours or even a number of days after drying of the building material, depending on the prevailing conditions, a hydrophobic zone is developed which surrounds the building material and drastically reduces its capillary water uptake. In the case of mass hydrophobizing, the aqueous solution of the organosiliconate is mixed, after further dilution where appropriate, with the aqueous slurry of, for example, a gypsum-based building material. Measurements of the water uptake of the gypsum building material after it has been cured and dried show a greatly reduced water uptake as compared with the unhydrophobized building material. The advantage of the mass hydrophobizing of gypsum, for example, is that the building material not only is surrounded by a hydrophobic zone but is water-repellent through and through. This is especially important with building materials which have a tendency to be water-soluble, such as gypsum, or if the building material is cut into pieces after the water repellency treatment. This technique is employed, for example, in the production of plasterboard panels, gypsum wallboarding panels or gypsum fiberboard panels.

Gypsum plasters and gypsum filling compounds or gypsum-based tile adhesives, however, are supplied to the building site as powders, in bags or silos, and are made up with water by stirring on site. For application in gypsum plasters, gypsum filling compounds, gypsum repair filler powders, gypsum-based tile adhesives and similar mineral building materials, therefore, a solid hydrophobizing agent is required that can be added to the ready-to-use dry mixture and which develops its hydrophobizing effect in a short time only on addition of water during application on site, such as on the building site, for example. This is called dry-mix application.

The majority of conventional dry-mix hydrophobizing agents in accordance with the current state of the art are supported systems, which means that a hydrophobizing agent which is in fact in liquid form, such as an active silane and/or siloxane ingredient, for example, is applied to a support material which is more or less chemically inert. The amount of hydrophobizing agent applied in this case is only such as to produce a dry and free-flowable powder. This produces active contents of only 30-50%—it follows from this that the mass of the inactive support material accounts for 50-70% of the total mass. The support material may be inorganic—examples are silicas and silicates—or organic—examples are polyvinyl alcohols, as described in WO 2010052201. By combination with the water used for making up the mix, and by intensive mixing, the liquid hydrophobizing agent develops its effect, while the support material remains in the cured building material as a functionless filling material. The support material may even have adverse effects on the fully cured building material—it is known, for instance, that polyvinyl alcohols tend to increase the hydrophilicity of gypsum building materials, which is counterproductive.

Conventional dry-mix hydrophobizing agents have a series of disadvantages. With these known products, a problem which occurs is that the high hydrophobicity of the powders and premature migration of the hydrophobizing agent onto the building material which is still to be mixed with water results in a delayed initial miscibility. As a result, in addition to the loss of time, unwanted dust is formed from the building material as a result of the delayed wetting with water. Likewise, conventional dry-mix hydrophobizing agents have a comparatively low active content, because they usually consist of a liquid active siloxane ingredient on a solid support, as described in WO 2010052201, example 1. Apart from its support activity, the support has no importance, and an increase in the active content would lead to sticky dry-mix hydrophobizing agents which would no longer be free-flowable. As a consequence, these hydrophobizing agents are not efficient enough.

U.S. Pat. No. 2,567,110 describes access to neutral (poly) siloxanes, starting from alkali metal sil(ox)anolates and chlorosilanes. Example 1 describes the preparation of sodium methylsiliconate by reaction of a monomethylsiloxane hydrolyzate with one molar equivalent of aqueous sodium hydroxide solution in the presence of ethanol. The solid is isolated by distillative removal of the solvent, and then dried to constant weight at 170° C. On the industrial scale, a process of this kind for isolating the solid is impracticable, since evaporation is accompanied by formation of firmly adhering crusts on the walls of the reaction vessel.

A further disadvantage of evaporation in the context of isolating the solid is the fact that alkali metal siliconates undergo thermal decomposition, which represents a reaction safety problem. For example, potassium methylsiliconate (K:Si=1:1) undergoes decomposition at above 120° C. in a highly exothermic reaction of 643 J/g with loss of the methyl group. Under adiabatic conditions, the temperature in this case rises to more than 300° C. (see comparative example 1).

Furthermore, starting from aqueous solutions of the alkali metal siliconates, a very large amount of energy is needed for the evaporation of the water solvent, and this impacts the economics of the process.

Siliconate powders are described in U.S. Pat. No. 2,438,055, U.S. Pat. No. 2,803,561, and DE 1176137. The siliconate powders described therein are in principle suitable as dry-mix hydrophobizing agents. However, the hydrophobizing effect is too low and the production processes are not suitable, particularly for industrial manufacture.

U.S. Pat. No. 2,438,055 describes the preparation of siliconates as hydrates in solid form. In that patent, the hydrolyzate of a monoorganotrialkoxysilane or of a monoorganotrichlorosilane is reacted with 1-3 mol equivalents of alkali metal hydroxide in the presence of alcohol. The siliconates, obtained in the form of hydrates, are crystallized by evaporation of the alcohol or by addition of corresponding nonpolar solvents.

In example 1, the preparation of solid sodium methylsiliconate hydrates is described: 1 mol equivalent of methyltriethoxysilane is reacted with 1 mol equivalent of sodium hydroxide in the form of saturated aqueous sodium hydroxide solution (i.e. 50% by weight). To crystallize the siliconate, methanol is added to the solution. Evidently only a portion of the siliconate is precipitated in this procedure. Indeed, by evaporation of the mother liquor, a further solid is isolated, which shows a 21% weight loss when dried over $P_2O_5$ at 140° C. Nothing is said about the proportions.

U.S. Pat. No. 2,803,561 subjects alkyltrichlorosilane to hydrolysis to give the corresponding alkylsilicic acid, which is subsequently reactive with alkali metal hydroxide to give an aqueous solution of alkali metal siliconate, which is stabilized by addition of up to 10% of alcohol or ketone. How the siliconate is dried is not described. The application of the dried siliconate for hydrophobizing gypsum is mentioned.

DE 1176137 describes the preparation of alkali methylsiliconate by reaction of methyltrichlorosilane with aqueous NaOH. The alkali methylsiliconate is acidified with methyltrichlorosilane, and the resultant methylsilicic acid is precipitated, washed NaCl-free, dried, and reacted again with NaOH to give a 30% strength Na alkali metal methylsiliconate solution, which is dried at 400° C. in 2 minutes to give the siliconate powder.

SUMMARY OF THE INVENTION

The invention provides powders (P) comprising salts of organosilanols, of their hydrolysis/condensation products, or of organosilanols together with their hydrolysis/condensation products and cations selected from alkali metal ions, ammonium ions, and organoammonium ions, wherein the molar ratio of cation to silicon is 0.1 to 0.89, and also a process for their industrial production.

DETAILED DESCRIPTION OF THE PREFERRED EMBODIMENTS

The powders (P) are free-flowable and storable and form stable aqueous solutions with water. The powders (P) can be produced in a safe and reliable process which is easy to implement industrially.

The invention also provides a process for producing powders (P1), by subjecting in a first step organosilanes of the general formula 1

$$(R^1)_a Si(Y)_b(-Si(R^2)_{3-c}(Y)_c)_d \tag{1}$$

or their hydrolysis/condensation products, or the organosilanes of the general formula 1 together with their hydrolysis/condensation products, where $R^1$ and $R^2$ are each a monovalent, Si—C-bonded hydrocarbon radical which is unsubstituted or is substituted by halogen atoms, amino groups or $C_{1-6}$ alkyl- or $C_{1-6}$ alkoxy-substituted silyl groups and has 1 to 30 carbon atoms, in which one or more nonadjacent —$CH_2$— units may be replaced by groups —O—, —S—, or —$NR^3$—, and in which one or more nonadjacent =CH— units may be replaced by groups —N=, $R^3$ is hydrogen or a monovalent hydrocarbon radical having 1 to 8 carbon atoms which is unsubstituted or substituted by halogen atoms or $NH_2$ groups, Y is hydrogen, F, Cl, Br, or $OR^4$, $R^4$ is a monovalent hydrocarbon radical which is unsubstituted or substituted by halogen atoms or silyl groups and has 1 to 10 carbon atoms, in which one or more nonadjacent $CH_2$ units may be replaced by groups —O—, —S—, or —$NR^3$—, and in which one or more nonadjacent =CH— units may be replaced by groups —N=, a denotes the values 1, 2 or 3, and b, c, and d denote the values 0, 1, 2 or 3, with the proviso that b+c≥1 and a+b+d=4, to hydrolysis in the presence of water and one or more basic salts of cations selected from alkali metal ions, ammonium ions, and organoammonium ions, the amount of basic salt being calculated such that per mole of silicon there is at least 0.1 mol and not more than 3 mol of cations, and, if the organosilanes of the general formula 1 contain radicals selected from F, Cl, and Br, a further mole of basic salt is present per mole of F, Cl, and Br, and at least 50% of the radicals $R^1$ and $R^2$ contain not more than 3 C atoms, in a second step, removing the liberated compound HY, during or after the hydrolysis reaction, from the reaction mixture, in the form of vapor and/or gas, in the presence of a liquid F which is inert under the reaction conditions, has a boiling point above that of the liberated compound HY, and has a solvency of not more than 1% by weight for the siliconate salt produced in solid form, at 100° C./1 bar, in a third step, removing water by distillation to form a suspension of the siliconate salt in the liquid F, and in a fourth step, isolating the siliconate salt in the form of powder (P1) by filtration, centrifugation, sedimentation or evaporation of the inert liquid F.

The invention also provides the powders (P1) producible by this process.

The powders (P) are preferably also produced by this process.

The powders (P) have a water solubility at 20° C. of preferably at least 20% by weight, more preferably at least 30% by weight, and most preferably at least 40% by weight.

In the powder (P) the preferred molar ratio of cation to silicon is at least 0.2, preferably at least 0.4, more preferably at least 0.5, and not more than 0.85, more preferably not more than 0.75, and most preferably not more than 0.7. The cation is preferably selected from sodium and potassium. The powder (P) is preferably a methylsiliconate.

The powders (P) and (P1) preferably have average particle sizes of not more than 500 µm, more preferably not more than 300 µm, and most preferably not more than 200 µm.

The water removed by distillation in the third step comes from the water added in the first step and from water produced by condensation processes. In the third step, the inert liquid F may serve as an azeotrope-former for the distillative removal of water.

The individual steps in the process of the invention need not run separately one after another in terms of time, strictly speaking, but instead, depending on the nature of the substances employed, are designed in such a way that, in order to maximize the space/time yield, they run largely parallel or at least flow seamlessly into one another.

In place of the monomeric compounds of general formula 1 it is possible to use not only mixtures of silanes of the general formula 1 but also their hydrolysis/condensation products, which are formed, for example, by partial hydrolysis of the monomeric silanes or by alcoholysis of the corresponding chlorosilane precursors with moist alcohol, and optionally in a mixture with the respective monomers.

In the case of the silanes of the general formula 1, for a rapid and complete reaction, a certain fraction of unhydrolyzed and/or condensed monomers is preferred, and so the mixture as a whole preferably contains at least 60%, more preferably at least 80%, and most preferably at least 90% of all of its silicon-containing constituents in monomeric form. Tolerable oligomer fractions arise when, for example, the alcohol $HOR^4$, removed by distillation in the second step of the process of the invention, already contains certain fractions of water and is used again for preparing the alkoxysilanes. The establishment of a recycle circuit in terms of substances significantly increases the economics of the overall procedure.

It is possible as well to use mixed oligomers of compounds of the general formula 1, or mixtures of these mixed oligomeric siloxanes with monomeric silanes of the general formula 1. Any silanol groups, formed by hydrolysis, that are present in the compounds of the general formula 1 or their oligomers are no disruption.

It is preferably the case that for not more than 10 mol %, more particularly not more than 1 mol %, of the compounds of the general formula 1, Y is hydrogen.

$R^1$ and $R^2$ may be linear, branched, cyclic, aromatic, saturated, or unsaturated. Examples of amino groups in $R^1$ and $R^2$ are radicals $-NR^5R^6$, where $R^5$ and $R^6$ may be hydrogen or a $C_1$-$C_8$-alkyl, cycloalkyl, aryl, arylalkyl or alkylaryl radical, which may be substituted by $-OR^7$, where $R^7$ may be $C_1$-$C_8$-alkyl, aryl, arylalkyl or alkylaryl. If $R^5$ and $R^6$ are alkyl radicals, nonadjacent $CH_2$ units therein may be replaced by groups $-O-$, $-S-$, or $-NR^3-$. $R^5$ and $R^6$ may also constitute a ring system. $R^5$ is preferably hydrogen or an alkyl radical having 1 to 6 carbon atoms.

$R^1$ and $R^2$ in the general formula 1 are each preferably a monovalent hydrocarbon radical having 1 to 18 carbon atoms which is unsubstituted or substituted by halogen atoms or by amino, alkoxy or silyl groups. Particularly preferred are unsubstituted alkyl radicals, cycloalkyl radicals, alkylaryl radicals, arylalkyl radicals, and phenyl radicals. The hydrocarbon radicals $R^1$ and $R^2$ preferably have 1 to 6 carbon atoms. Particularly preferred are the methyl, ethyl, propyl, 3,3,3-trifluoropropyl, vinyl, and the phenyl radical, especially the methyl radical.

Further examples of radicals $R^1$ and $R^2$ are as follows: n-propyl, 2-propyl, 3-chloropropyl, 2-(trimethyl-silyl)ethyl, 2-(trimethoxysilyl)ethyl, 2-(triethoxy-silyl)ethyl, 2-(dimethoxymethylsilyl)ethyl, 2-(diethoxymethylsilyl) ethyl, n-butyl, 2-butyl, 2-methylpropyl, tert-butyl, n-pentyl, cyclopentyl, n-hexyl, cyclohexyl, n-heptyl, n-octyl, 2-ethylhexyl, n-nonyl, n-decyl, n-undecyl, 10-undecenyl, n-dodecyl, isotridecyl, n-tetradecyl, n-hexadecyl, vinyl, allyl, benzyl, p-chlorophenyl, o-(phenyl)phenyl, m-(phenyl)-phenyl, p-(phenyl)phenyl, 1-naphthyl, 2-naphthyl, 2-phenylethyl, 1-phenylethyl, 3-phenylpropyl, 3-(2-aminoethyl)aminopropyl, 3-aminopropyl, N-morpholino-methyl, N-pyrrolidinomethyl, 3-(N-cyclohexyl)-aminopropyl, 1-N-imidazolidinopropyl radical.

Further examples of $R^1$ and $R^2$ are radicals $-(CH_2O)_n-R^9$, $-(CH_2CH_2O)_m-R^9$, and $-(CH_2CH_2NH)_oH$, where n, m and o denote values from 1 to 10, more particularly 1, 2, or 3, and $R^6$ and $R^9$ have the definitions of $R^5$ and $R^6$.

$R^3$ is preferably hydrogen or an alkyl radical having 1 to 6 carbon atoms which is unsubstituted or substituted by halogen atoms. Examples of $R^3$ are listed above for $R^1$.

$R^4$ in the general formula 1 may have ethylenically unsaturated double bonds or be saturated. Preference is given to a monovalent alkyl radical having 1 to 4 carbon atoms which is optionally substituted by alkoxy groups having 1 to 3 carbon atoms and may be linear or branched. The radicals in question are preferably linear alkyl radicals, more preferably the methyl and ethyl radicals, and most preferably the methyl radical.

Further examples of radicals $R^4$ are as follows: n-propyl, 2-propyl, n-butyl, 2-butyl, 2-methylpropyl, tert-butyl, 2-(methoxy)ethyl, 2-(ethoxy)ethyl radical, 1-propen-2-yl radical.

If d=0, then the fraction of compounds of the general formula 1 for which a=2 or 3, optionally their hydrolysis/condensation products, or their fraction in mixed hydrolysis/condensation products with silanes of the general formula 1 where a=1, is preferably such as to produce solids of which at least 20 g, preferably at least 40 g, more preferably at least 50 g dissolve in 50 g of demineralized water at 20° C. to give a clear solution, and the fraction is preferably 0 to 20 mol %, more preferably 0 to 10 mol %, more particularly 0 mol %, based on the total amount of silane of the general formula 1 and/or its hydrolysis/condensation products. Preferably, d is 0. In preferably not more than 20 mol %, and more preferably not more than 5 mol % of the compounds of the general formula 1, d has a value of 1, 2 or 3.

Examples of compounds of the general formula 1 where a=1 are as follows:

MeSi(OMe)$_3$, MeSi(OEt)$_3$, MeSi(OMe)$_2$(OEt). MeSi(OMe)(OEt)$_2$, MeSi(OCH$_2$CH$_2$OCH$_3$)$_3$, H$_3$C—CH$_2$—CH$_2$—Si(OMe)$_3$, (H$_3$C)$_2$CH—Si(OMe)$_3$, CH$_3$CH$_2$CH$_2$CH$_2$—Si(OMe)$_3$, (H$_3$C)$_2$CHCH$_2$—Si(OMe)$_3$, tBu-Si(OMe)$_3$, PhSi(OMe)$_3$, PhSi(OEt)$_3$, F$_3$C—CH$_2$—CH$_2$—Si(OMe)$_3$, H$_2$C=CH—Si(OMe)$_3$, H$_2$C=CH—Si(OEt)$_3$, H$_2$C=CH—CH$_2$—Si(OMe)$_3$, Cl=CH$_2$CH$_2$CH$_2$—Si(OMe)$_3$, cy-Hex-Si(OEt)$_3$, cy-Hex-CH$_2$—CH$_2$—Si(OMe)$_3$, H$_2$C=CH—(CH$_2$)$_9$—Si(OMe)$_3$, CH$_3$CH$_2$CH$_2$CH$_2$CH(CH$_2$CH$_3$)—CH$_2$—Si(OMe)$_3$, hexadecyl-Si(OMe)$_3$, Cl—CH$_2$—Si(OMe)$_2$, H$_2$N—(CH$_2$)$_3$—Si(OEt)$_2$, cyHex-NH—(CH$_2$)$_3$—Si(OMe)$_3$, H$_2$N—(CH$_2$)$_2$—NH—(CH$_2$)$_3$—Si(OMe)$_3$, O(CH$_2$CH$_2$)$_2$N—CH$_2$—Si(OEt)$_3$, PhNH—CH$_2$—Si(OMe)$_3$, hexadecyl-SiH$_3$, MeSi(OEt)$_2$H, PhSi(OEt)$_2$H, PhSi(OMe)$_2$H, MeSi(OEt)H$_2$, propyl-Si(OMe)$_2$H, MeSiH$_3$, MeSi(OEt)(OMe)H, (MeO)$_3$Si—CH$_2$CH$_2$—Si(OMe)$_3$, (EtO)$_3$Si—CH$_2$CH$_2$—Si(OEt)$_3$, Cl$_3$Si—CH$_2$CH$_2$—SiMeCl$_2$, Cl$_3$Si—CH$_2$CH$_2$—SiCl$_3$, Cl$_3$Si—(CH$_2$)$_6$—SiCl$_3$. (MeO)$_3$SiSi(OMe)$_2$Me, MeSi(OEt)$_2$ Si(OEt)$_3$, MeSiCl$_2$SiCl$_3$, Cl$_3$SiSiCl$_3$, HSiCl$_2$SiCl$_2$H, HSiCl$_2$SiCl$_3$, MeSiCl$_3$, MeSiCl$_2$H, H$_2$C=CH—SiCl$_3$, PhSiCl$_3$, F$_3$C—CH$_2$—CH$_2$—SiCl$_3$, Cl—CH$_2$CH$_2$CH$_2$ SiCl$_3$, MeSi(OMe)Cl$_2$, MeSi(OEt)ClH, EtSiBr$_3$, MeSiF$_3$, Cl—CH$_2$—SiCl$_3$, Cl$_2$CH—SiCl$_9$.

Preference is given to MeSi(OMe)$_3$, MeSi(OEt)$_3$, (H$_3$C)$_2$CHCH$_2$—Si(OMe)$_3$ and PhSi(OMe)$_3$, with methyltrimethoxysilane and/or its hydrolysis/condensation product being preferred.

Examples of compounds of the general formula 1 where a=2 are as follows:

Me$_2$Si(OMe)$_2$, Me$_2$Si(OEt)$_2$, Me$_2$Si(OCH(CH$_3$)$_2$)$_2$, MeSi(OMe)$_2$CH$_2$CH$_2$CH$_3$, Et$_2$Si(OMe)$_2$, Me$_2$Si(OCH$_2$CH$_2$OCH$_3$)$_2$MeSi(Ome)$_2$Et, (H$_3$C)$_2$CH—Si(OMe)$_2$Me, Ph-Si(OMe)$_2$Me, t-Bu-Si(OMe)$_2$Me, Ph$_2$Si(OMe)$_2$, PhMeSi(OEt)$_2$, MeEtSi(OMe)$_2$, F$_3$C—CH$_2$—CH$_2$—Si(OMe)$_2$Me, H$_2$C=CH—Si(OMe)$_2$Me, H$_2$C=CH—CH$_2$—Si(OMe)$_2$Me, Cl—CH$_2$CH$_2$CH$_2$—Si(OMe)$_2$Me, cy-Hex-Si(OMe)$_2$Me, cy-Hex-CH$_2$—CH$_2$—Si(OMe)$_2$Me, H$_2$C=CH—(CH$_2$)$_9$—Si(OMe)$_2$Me, Cl—CH$_2$—SiMe(OMe)$_2$, H$_2$N—(CH$_2$)$_3$—SiMe(OEt)$_2$, cyHex-NH—(CH$_2$)$_3$—SiMe(OMe)$_2$, H$_2$N—(CH$_2$)$_2$—NH—(CH$_2$)$_3$—SiMe(OMe)$_2$, O(CH$_2$CH$_2$)$_2$N—CH$_2$—SiMe(OMe)$_2$, PhNH—CH$_2$—SiMe(OMe)$_2$, (MeO)$_2$MeSi—CH$_2$CH$_2$—SiMe(OMe)$_2$, (EtO)$_2$MeSi—CH$_2$CH$_2$—SiMe(OEt)$_2$, Cl$_2$MeSi—CH$_2$CH$_2$—SiMeCl$_2$, Cl$_2$MeSi—CH$_2$—SiMeCl$_2$, (MeO)$_2$MeSiSi(OMe)$_2$Me, MeSi(OEt)$_2$SiMe(OEt)$_2$, MeCl$_2$SiSiMeCl$_2$, HClMeSiSiMeClH, Me$_2$SiCl$_2$, Me$_2$SiClH, H$_2$C=CH—SiMeCl$_2$, Ph$_2$SiCl$_2$, MePhSiCl$_2$, F$_3$C—CH$_2$—CH$_2$—SiMeCl$_2$, Cl—CH$_2$CH$_2$CH$_2$—SiMeCl$_2$, Me$_2$Si(OMe)Cl, Me$_2$Si(OEt) H, EtSiMeBr$_2$, Me$_2$SiF$_2$, Cl—CH$_2$—SiMeCl$_2$, Cl$_2$CH—SiMeCl$_2$, Me$_2$Si(OEt)H, Me$_2$SiH$_2$, Et$_2$SiH$_2$, EtMeSiH$_2$, Ph$_2$SiH$_2$, Me$_2$Si(OMe)Si(OMe)$_3$, Me$_2$Si(OMe)Si(OMe)Me$_2$, hexadecyl-SiMeH$_2$, Me$_2$Si(OMe)SiMe$_3$, Me$_2$Si(OMe)SiMe(OMe)$_2$.

Preference is given to Me$_2$Si(OMe)$_2$, Me$_2$Si(OEt)$_2$, MeSi(OMe)$_2$CH$_2$CH$_2$CH$_3$, and Ph-Si(OMe)$_2$Me, with Me$_2$Si(OMe)$_2$ and MeSi(OMe)$_2$CH$_2$CH$_2$CH$_3$ being particularly preferred.

Me denotes the methyl radical, Et denotes the ethyl radical, Ph denotes the phenyl radical, t-Bu denotes the 2,2-dimethylpropyl radical, cy-Hex denotes the cyclohexyl radical, and hexadecyl denotes the n-hexadecyl radical.

It is important that at least 50%, preferably at least 60%, more preferably at least 70%, and not 100%, preferably not more than 90%, more preferably not more than 80% of all the radicals R$^1$ in the compounds of the general formula 1 or the hydrolysis/condensation products thereof are methyl radicals, ethyl radicals or propyl radicals.

The basic salts preferably have a pK$_b$ of not more than 12, more preferably not more than 10, and most preferably not more than 5. Basic salts used are compounds which form solvated hydroxide ions in water and comprise alkali metal ions or ammonium ions as their cations. Alkali metal salts used are preferably alkali metal hydroxides such as lithium hydroxide, sodium hydroxide, potassium hydroxide, and cesium hydroxide, more preferably sodium hydroxide and potassium hydroxide. Further examples of alkali metal salts are alkali metal carbonates such as sodium carbonate and potassium carbonate, and also alkali metal hydrogen carbonates such as sodium hydrogen carbonate, alkali metal formates such as potassium formate, alkali metal silicates (waterglass) such as sodium orthosilicate, disodium metasilicate, disodium disilicate, disodium trisilicate or potassium silicate. It is also possible furthermore to use alkali metal oxides, alkali metal amides or alkali metal alkoxides, preferably alkali metal alkoxides which release the same alcohol as the silanes of the general formula 1 that are used.

Preferred organoammonium ions are the cations of the monomeric amines of the general formula NR$_4$, in which at least one radical R represents an organic radical. R has the definitions and preferred definitions of R$^1$. Examples of ammonium ions of monomeric amines of the general formula NR$_4$ are Me$_4$N, Et$_4$N, nPr$_4$N, iPr$_4$N, nBu$_4$N, benzyl-NMe$_3$, dodecyl-NMe$_3$, and of the formulae H$_3$N—[CH$_2$CH$_2$—O—]$_q$—H and C$_{12}$H$_{25}$HN—{[CH$_2$CH$_2$—O—]$_4$—H}{[CH$_2$CH$_2$—O—]$_4$—H}.

Preferred organoammonium ions are, further, the cations of oligomeric or polymeric amines which have more than one amine function in the cation, as for example of general formulae H$_3$N—[CH$_2$]$_r$—NH$_3$Cl, where r denotes values from 1 to 10, and H$_3$N—[[CH$_2$]$_s$—NH]$_t$—[CH$_2$]$_s$—NH$_2$, where s denotes values from 1 to 6 and t denotes values from 1 to 10,000, more preferably up to 1000, and most preferably up to 100.

In the case of the oligomeric and polymeric amines, a part of the amine functions may be present in the form of hydrochloride, hydrogensulfate or phosphate.

As ammonium salts it is preferred to use the commercially available or readily preparable quaternary ammonium hydroxides, ammonium carbonates or ammonium alkoxides. In the case of water-soluble amines it is preferred to use aqueous solutions, since in aqueous solution the ammonium hydroxide is present in equilibrium with the free amine and hence the salt does not have to be isolated additionally.

Mixtures of different salts, possibly of different alkali metals, can also be used, examples being mixtures of sodium hydroxide and potassium hydroxide, and mixtures of alkali metal salts and ammonium salts as well, examples being mixtures of alkali metal hydroxides and ammonium salts, such as, for example, potassium hydroxide and ethanolamine or sodium carbonate and tetramethylammonium hydroxide. Typical accompanying constituents in technical grades of the basic salts (i.e., at purities between 80% and 99% by weight), such as water or other salt fractions, such as sodium fractions in potassium salts or carbonates in hydroxides, for example, are generally no disruption, and can be tolerated. Another preferred variant is the use of aqueous preparations of alkali metal siliconates optionally in a mixture with other alkali metal salts, preferably alkali metal hydroxides. This may be advantageous if the aqueous siliconate preparation (solution, suspension, emulsion) is already produced as a commercial product in large quantities, for example, hence necessitating merely one further reaction step in order to produce the powders (P1).

The amount of basic salt is preferably selected such that the molar ratio of cation to silicon is at least 0.2, preferably at least 0.4, more preferably at least 0.5, and most preferably at least 0.6, and not more than 0.9, preferably not more than 0.85, more preferably not more than 0.75, and most preferably not more than 0.7.

In the presence of radicals selected from F, Cl, and Br in the general formula 1, the amount of F, Cl, and Br present is reacted with the stoichiometric amount of base, preferably with alkali metal hydroxide. The resultant neutralization products are impossible or very difficult to separate from the organosiliconate, and therefore preferably remain in the powder (P1) of the invention, thereby reducing its active ingredient content accordingly. Preferably, therefore, not more than 50 mol %, more preferably not more than 20 mol %, and most preferably not more than 5 mol %, of the compounds of general formula 1 have fluorine, chlorine and/or bromine as Y.

One advantage of the process of the invention is the massive breadth in variation of substances employed that can be tolerated, and the associated relatively low requirements concerning their purity. For this reason, the process is very well suited to deriving value from secondary products and waste products from the overall silane/siloxane system—for example, residues from the direct silane synthesis, partially alkoxylated chlorosilane mixtures, by-products of hydrosilylations, catalyst-containing distillation residues, condensates from CVD operations, and many more. There may also be liquid, solid or gaseous impurities or by-products present, which, provided they cause no disruption, may remain in the product—for example, silica or metal salts, such as iron chloride, iron oxide, aluminum oxide or platinum-containing catalysts—or can easily be removed by the process—such as solvents.

The amount of water used preferably corresponds to the amount required for complete hydrolysis of the radicals Y, optionally reduced by the amount of HY eliminable from the basic salt used and also by the amount of water optionally bound in the alkali metal salt, ammonium salt or organoammonium salt, or optionally water formed in condensation processes. Although chemically there is no upper limit on the amount of water, the water fraction should be minimized on economic grounds, since excess water has to be removed again. Owing to the greater ease of metering solutions of the basic salt rather than solids, the desired amount of basic salt is preferably used in solution in the required amount of water. An excess of water, accordingly, will be sensible and acceptable when, for example, the low solubility of the basic salt in water necessitates a greater amount of water for producing a saturated solution than is needed for the hydrolysis in the context of the process of the invention, or when the salt solution is available industrially in a corresponding concentration. An excess of water may also serve to accelerate the hydrolysis reaction and/or to reduce any possible residual fraction of unhydrolyzed radicals Y in the powder P or P1.

One possibility to reduce the fraction of water is to add the basic salt or basic salt mixture either in pure form as a solid or as a solution in an organic solvent, preferably in the same alcohol which, where appropriate, is liberated during the hydrolysis reaction, and to meter in separately the minimum amount of water that is required. This variant is appropriate when using hydrolyzable alkali metal alkoxides, ammonium alkoxides, ammonium hydroxides or alkali metal amides as basic salt. However, combinations of different solvents may also be employed, such as mixtures of water and alcohol, of alcohol, amine, and water, or of amine and water, for example.

Under the reaction conditions, the inert liquid F does not intervene in the reaction. The boiling point of the inert liquid F at 1013 hPa is preferably at least 10° C. and more preferably at least 30° C. above the boiling point of the compound HY released in the second step.

Suitable inert liquids F are preferably hydrocarbons such as alkanes, cycloalkanes, aromatics or alkylaromatics, or mixtures thereof, and also ethers. Preference is given to using alkanes and alkane mixtures, cycloalkanes, and alkylaromatics, more preferably alkane mixtures. Advantageous qualities of alkane mixtures are their favorable price and their ready availability in a variety of defined boiling ranges.

Examples of liquids F include n-hexane, cyclohexane, n-heptane, cycloheptane, n-octane, cyclooctane, n-nonane, n-decane, n-dodecane, 2-methylheptane, methylcyclopentane, methylcyclohexane, isoparaffins such as Isopar® C, E, G, H, L, and M from ExxonMobil, benzene, toluene, o-xylene, m-xylene, p-xylene, mesitylene, ethylbenzene, methyl tert-butyl ether, diethyl ether, diphenyl ether, phenylmethyl ether, and di-n-butyl ether.

The proportion of the liquid F in the overall mixture is selected so as to ensure ready stirrability of the resulting suspension. This proportion is preferably at least 50% by weight, more preferably at least 100% by weight, and preferably not more than 500% by weight, more preferably not more than 300% by weight, of the expected amount of solids.

The silane of the general formula 1 and/or its hydrolysis/condensation products are preferably introduced initially, and basic salt and water are metered in, preferably in the form of an aqueous solution. Where some or all of Y are F, Cl, or Br, it may be more favorable to introduce basic salt and water initially.

To dissolve the reactants or to reduce the viscosity it may be advantageous to add a solvent. For this purpose it is preferred to add the alcohol $HOR^4$ which may be formed in any case in the reaction mixture in the course of the hydrolysis, or the inert liquid F. The reaction takes place customarily at a temperature of 0° C. to 150° C. and under the pressure of the surrounding atmosphere. The process may alternatively be carried out under a lower or higher pressure. The heat of reaction released during the hydrolysis may be utilized in order to heat the reaction mixture. The metering time is therefore guided primarily by the thermal performance from the reaction or by the cooling performance of the reactor. The thermal performance is usually not enough to bring mixtures to boiling and to accomplish complete distillative removal of any alcohol released. Preferably, therefore, heating to boiling is carried out during the metering or when metering is at an end, and the alcohol given off is removed by distillation. In order to maximize the space/time yield, the inert liquid F is preferably metered in at a rate such that the fill level of the reaction vessel remains constant, i.e., such that only the volume of alcohol removed by distillation is replaced by the liquid F. If the liquid F is immiscible with the alcohol that is given off, and has a lower specific weight than the alcohol, this procedure may be easily automated, for example, using a liquid separator which is filled with the inert liquid F before the alcohol distillate is collected. In this case, the amount of inert liquid running back into the reaction vessel is exactly the same as that of the alcohol removed by distillation. When the reaction has ended, the alcohol can be withdrawn via the bottom valve of the separator and used again, for example, for preparing the silanes of the general formula 1. In the case of this procedure, the progress of the hydrolysis reaction can be easily monitored by determining the amount of alcohol in the separator, by a volume or weight measurement, for example, and ascertaining the end point. Following distillative removal of the alcohol, the mixture is preferably heated to an extent such that residues of alcohol and water, and also any water formed in the course of condensation processes, are removed in circulation, while the siliconate precipitates as a solid. It is particularly preferred to conduct heating up to the boiling point of the inert liquid F. When a liquid separator is being used, the water collects as the lower phase in the distillate of liquid F, and so the drying procedure can likewise easily be monitored by checking the amount of water separated off.

If the liberated alcohol dissolves in the inert liquid F, it is preferred to carry out distillation without a liquid separator to the boiling point of the higher-boiling liquid F. An option is to carry out fractional distillation via a distillation column with appropriate separation performance, in order to separate alcohol, liquid F, and—optionally—water from one another distillatively. In this case the distillates obtained are typically mixtures of alcohol, liquid F, and—optionally—water, which may either be purified separately or used directly again for preparing the starting compounds. In this procedural variant it is preferred to top up with fresh liquid F during the distillation in an amount such in each case that the reaction mixture remains stirrable.

Where there is no alcohol present or no alcohol released in the reaction mixture, i.e., if Y=hydrogen, F, Cl and/or Br, there are gaseous cleavage products formed, namely hydrogen, HF, HCl, or HBr, and/or there are low-volatility salts formed that remain in the product, meaning that the inert liquid can be separated off immediately after reaction is at an end.

In a further preferred process variant, one suitable particularly for a continuous regime, a solution of the siliconate salt is prepared first of all, by reaction of the organosilanes of the general formula 1 (or their hydrolysis/condensation products, or by reacting the organosilanes of the general formula 1 together with their hydrolysis/condensation products), with basic salt in the presence of water (hydrolysis) (continuously, for example, by the method described in DE 4336600, preferably using the amount of water necessary at least for a hydrolysis, and without full distillative removal of the alcohol liberated). This is done preferably in the absence of the inert liquid F. In the second and third steps, carried out simultaneously, the siliconate salt solution formed is contacted with the inert liquid F under conditions in which the volatile constituents of the solution evaporate and the siliconate salt precipitates as a solid. The siliconate salt solution formed, which as well as the siliconate salt comprises further hydrolysis products such as alcohol or fluoride, chloride or bromide of the basic salt, and optionally excess water, is preferably mixed with the liquid F.

When the volatile constituents are removed by distillation, the solid siliconate salt is obtained as a suspension in the liquid F, and can be isolated in the fourth step by filtration, centrifugation, sedimentation or evaporation of the inert liquid F. In this case it is preferred to introduce the inert liquid F initially and to meter in the solution of the siliconate salt under conditions which ensure immediate evaporation of the volatile constituents. The conditions that are optimum in each particular case may be readily determined by the skilled person by varying the amount of liquid F, temperature, pressure and/or metering rate. If the solution for siliconate salt is contacted in finely divided form—via a nozzle, for example—with the inert liquid F, the evaporation procedure can be accelerated. It is preferred here to introduce the siliconate solution into the liquid F directly below the surface. To accelerate the evaporation process it is also possible for some of the volatile constituents of the metered siliconate salt solution to be drawn off or distilled off in an upstream step, in which case it is advisable on economic grounds, during the hydrolysis, to add only the amount of water necessary for a complete reaction. The siliconate salt particles formed directly during the metered introduction can be removed continuously from the reaction vessel, in the form of a suspension, and supplied to an optionally continuous solids isolation process. The liquid F can be recovered almost completely and used again in the procedure. By this means it is possible to keep sizes of apparatus and quantities of reserve liquid F (hold-up) low, in spite of correspondingly high throughput rates. Another positive effect of this version of the process is the short residence time of the siliconate solution under distillation conditions (preferably above room temperature), allowing even thermally unstable siliconate solutions to be converted completely and without decomposition phenomena into suspensions, which generally enjoy a relatively high thermal stability. Another advantage is that via the temperature of the liquid F during the metering of the siliconate salt solution it is possible to influence the particle size distribution of the siliconate salt particles formed. Generally speaking here, lower temperatures lead to a larger average particle size.

It is an advantage of the process of the invention that solid to pastelike accumulations on the mixing assemblies and the reactor wall detach during this procedure as the degree of drying progresses, and that a fine suspension is formed from which the powder (P1) can be isolated by simple solids separation such as filtration, sedimentation or centrifuging. In one preferred version the volatile constituents in the fine suspension are distilled off under the pressure of the surrounding atmosphere or under reduced pressure, and the resultant powder (P1) is dried. This takes place preferably at temperatures below the decomposition temperature of the suspension and/or of the dried solid, a temperature which requires individual determination (by DSC measurement, for example)—typically, then, at temperatures below 120° C., preferably below 100° C., more preferably below 80° C. This gentle drying prevents overheating and consequent uncontrollable decomposition reactions. The liquid F separated off in the solids isolation procedure can be used for rinsing the plant, in order to flush out final residues of solids, and to increase the yield. The solid, isolated in particular via filtration, sedimentation or centrifuging, can be further dried—preferably to constant weight—by passing optionally heated inert gas through the system, or else in a drying cabinet or heated mixer, optionally under reduced pressure.

The process can be carried out in batch operation, using—for example—a stirred tank or paddle dryer with top-mounted distillation attachment, of the kind customary in multipurpose plants. Owing to the low level of fouling, it is usually not necessary in the course of production campaigns to clean the reactor between the individual batches of solids residues. Should cleaning nevertheless be necessary, at the end of the campaign, for example, it is easily possible, inexpensively and without harmful emissions, by simple flushing or optionally flooding of the plant with water, owing to the good water solubility. A continuous process in a tube reactor or in a mixing/conveying assembly such as a kneading apparatus or a single-screw or twin-screw extruder or horizontal paddle dryer—preferably with a plurality of chambers for the various process steps is likewise possible and is advantageous for industrial production.

The powders (P) and (P1) are very suitable for use as hydrophobizing agents, more particularly for mineral substrates and building materials, natural fibers, such as cellulose and wool, and synthetic fibers. The hydrophobizing of processed fibers, such as textiles, paper, and cardboard, is likewise a ready possibility. Among the mineral building materials, gypsum-based building materials are preferred that contain preferably at least 10% and more preferably at least 20% by weight of gypsum.

Among the gypsums, those known as reactive gypsums are preferred: calcium sulfate hemihydrate ($CaSO_4.0.5\ H_2O$), in the form, for example, of building plaster, stucco plaster, plaster of Paris or insulating plaster, and anhydrites ($CaSO_4$, anhydrite II and III), as are obtained from known calcining processes, starting from natural gypsum or synthetic gypsums. In the calcining processes, the calcium sulfate dihydrate, calcium sulfate hemihydrate, and anhydrite phases may be obtained, in their various forms, in different proportions. Other kinds of plaster as well, such as screeding plaster, imitation marble, anhydrite, and synthetic plasters (obtained in flue gas desulfurization, in the production of phosphoric acid and hydrofluoric acid, or of organic carboxylic acids) are highly suitable. Depending on the target application (e.g., gypsum plasterboard, gypsum wallboarding panel, gypsum plaster, filling compound, screeding plaster, etc.) and region of mining or source, gypsums with different compositions are used as raw materials, although often it is only the term "gypsum-based building material" that is used. The gypsum may comprise additives which facilitate the production of gypsum moldings or gypsum products, or which enhance the qualities of the gypsum moldings and gypsum products. Examples of additives are fillers such as silicon dioxide, calcium carbonate, and fibers, accelerators such as calcium sulfate dihydrate, potassium sulfate, or aluminum sulfate, retardants such as proteins or salts of tartaric acid or of citric acid, plasticizers and water reducers for the gypsum slurry such as melamine-, naphthalene- or ligno-sulfonates or polycarboxylates, adhesion promoters for cardboard such as starches, adhesion promoters for plasters and filling compounds such as redispersible polymer powders, pH modifier additives such as hydrated lime, for example, or cements.

Preference is given to the hydrophobizing of building-material powders, more particularly gypsum-based building materials. The powders (P) and (P1) are used more particularly as dry-mix hydrophobizing agents.

The powders (P) and (P1) are initially water-wettable (hydrophilic) and result in a building-material powder whose mixing qualities are very good and unimpaired. The powders then rapidly develop hydrophobicity over time, which is required for setting by the building material, such as a gypsum plaster, a gypsum filling compound, or a gypsum-based tile adhesive, for example, and they therefore exhibit an excellent balance between hydrophilicity and hydrophobicity. In their mechanism of action they do not release any volatile organic compounds (VOCs). As a result of this and of the fact that they contain no deliberately added support materials, they are among the most efficient gypsum hydrophobizing agents available and among the most efficient dry-mix hydrophobizing agents.

The pH of the gypsum in question is unimportant for the hydrophobizing effect. Gypsum powder mixtures with a neutral pH of 7 can be used, as can gypsum powder mixtures with an acidic pH between 3-7, and gypsum powder mixtures with an alkaline pH between 7-13. For use in mixtures with high pH levels, preference is given to blends of methylsiliconate with siliconates based on higher alkyl radicals, or to siliconates prepared from mixtures of different silanes of the general formula 1 where at least some of the radicals $R^1$ and $R^2$ contain more than one C atom. Preferred here is the combination of alkali metal methylsiliconates with alkali metal ethyl- and/or alkali metal propylsiliconates, or alkali metal siliconates prepared from mixtures of silanes of the general formula 1 where the radicals $R^1$ and $R^2$ are a methyl radical, and silanes of the general formula 1 in which the radicals $R^1$ and $R^2$ are methyl and propyl radicals, with preferably at least 20 mol % and more particularly at least 40 mol % of the organic radicals in the powder (P) or radicals $R^1$ and $R^2$ in the powder (P1) having at least 3 carbon atoms.

The powders (P) and (P1) are not only suitable as dry-mix hydrophobizing additives; they are likewise suitable for hydrophobizing other gypsum building materials from industrial manufacture wherein liquid hydrophobizing agents have been used to date. These include, very particularly, gypsum fiberboard panels, in which organic or inorganic fibers are added to the gypsum powder or gypsum slurry for mechanical reinforcement, and gypsum blocks or wallboarding panels, which are bonded by means of plaster bonding mortars to form solid walls in dry construction, in a manner similar to bricks.

It is likewise possible to provide plaster of Paris powders with water repellency using powders (P) and (P1), in order to provide statues, figures, ornaments, specialty components, impression moldings, and other plaster-based specialist fabrications, in the domestic or other spheres, with resistance to any influence of water.

The possibilities of using alkali metal methylsiliconate solutions for the production of gypsum plasterboard had to date been limited. As a result of the high pH of the siliconate solutions, detachment of the cardboard from the plaster core may occur even during production. With the powders (P) and (P1), obtained by the production procedure of the invention, it has been possible, however, to achieve a significant reduction in the alkali metal hydroxide content, resulting in a lower pH in the gypsum slurry. This presents an advantage for use in pH-sensitive applications, where it was hitherto impossible to use alkali metal methylsiliconate solutions. In the case of a pH-neutral alabaster plaster, the addition of 2% of potassium methylsiliconate in aqueous solution (SILRES® BS 16 from Wacker Chemie AG) leads to a pH increase from pH 7 to pH 12, while the addition of 0.8% of potassium methylsiliconate powder (molar ratio of potassium to silicon: 0.64) leads only to an increase from pH 7 to pH 11 (measured using indicator sticks), with a water uptake of below 5% being achieved in both cases. The additional restriction arising from the relatively low active ingredient content of the siliconate solutions as compared, for example, with silicone fluids based on polymethylhydrogensiloxane (e.g., SILRES® BS 94 from Wacker Chemie AG), which have an active ingredient content of around 100%, can likewise be eliminated, especially for the production of gypsum plasterboard, by using the powders (P) and (P1). For production-associated reasons, 40-60% of commercial siliconate solutions consist of water, which is not the case with the powders (P) and (P1). They consist preferably (i.e., in the case of Y F, Cl, Br) completely of active ingredient, and do not contain any water. Nevertheless, in contrast to the customary organic hydrophobizing powders, they have no tendency to undergo dust explosion, which is a further key advantage for safe handling, in connection, for example, with dry-mix production in air. In order to attenuate still further the increase in the pH after addition of the alkali metal methylsiliconate powder in applications that are even more pH-sensitive, and also in the production of gypsum plasterboard, the possibility exists of admixing the powders (P) and (P1) with acidic, pH reducing or buffering additives in solid form, which become active only when water is added in the application. In the case of liquid alkali metal methylsiliconate solutions, this approach is not conceivable, since in aqueous solution there would be a spontaneous neutralization reaction even before the application, and the alkali metal methylsiliconate would be destabilized and deactivated. Acidic additives of this kind may be all substances which provide a buffering or acidically reacting effect in the presence of water, and which can be isolated in solid form or are encapsulated in hydrolyzable or water-soluble coating substances such as polyvinyl alcohol, gelatin or polysaccharides (e.g., cyclodextrins), examples of such substances being hydrogensulfates, sulfuric esters, phosphates, hydrogenphosphates, dihydrogenphosphates, phosphoric esters and phosphorous esters, iron salts such as iron chloride, aluminum salts such as aluminum sulfate or aluminum nitrate, acidic clay earths, zeolites, silica gels, ion exchangers, long-chain monobasic or polybasic carboxylic acids and also their alkyl or silyl esters or their anhydrides, ammonium salts or phosphonium salts, acidically reacting organic compounds such as vitamin C (ascorbic acid), phenols, alginic acid or sulfonic acids and esters thereof, amidosulfonic acids, taurine, aminocarboxylic acids such as glycine, glutamic acid, or cysteine, phosphoric acids and their esters, aminophosphonic acids, sulfinic acids and their esters, polyacrylic and polymethacrylic acids, lactones, or sultones.

The powders (P) and (P1) may also be used in combination with other common hydrophobizing additives. For example, they reinforce the hydrophobizing effect of methylhydrogenpolysiloxane-based silicone fluids (e.g., SILRES® BS 94 from Wacker Chemie AG) in conveyor-line gypsum (used for gypsum plasterboard panels, for example).

The powders (P) and (P1) are likewise suitable for hydrophobizing building materials comprising other hydraulically setting binders, such as cements (Portland, aluminate, blast furnace, magnesia, or phosphate cement), waterglass, or lime. Accordingly the powders (P) and (P1) may find application in systems including masonry and adhesive mortars, base renders and decorative renders, tile adhesives, jointing mortars, adhesive mortars and reinforcing mortars for TICS systems, powder paints, cementitious sealing slurries, filling compounds, self-leveling flooring compounds and screeds, and also patching and repair mortars.

Presently in use for the water-repelling impregnation of neutral to slightly alkaline building materials, especially products made of fired clay or natural stone, are dilute solutions of alkali metal alkylsiliconates. Here, a highly diluted aqueous solution is produced from a water-containing concentrate (e.g., SILRES® BS 16 from Wacker Chemie AG), and is diluted with water in a production works for application at the works, or by a formulator for treatment of architectural facings, for production of primers, or for do-it-yourself application. The powders (P) and (P1) offer the advantage here that instead of the water-containing concentrate it is possible to supply the end user with a powder in 100 percent form, which can then likewise be adjusted, by dissolution in water, to the desired degree of dilution of the solution. In this way it is possible to achieve marked reductions in transport and stockholding costs.

This advantage is likewise manifested for the application of alkali metal alkylsiliconates in borehole injection for establishing dryer conditions in masonry, where the injection of hydrophobizing agents (e.g., diluted potassium methylsiliconate solutions) with and without pressure into existing masonry produces horizontal barriers against rising damp.

Alkali metal alkylsiliconates are likewise used as hydrophobizing additives in silicone resin paints. Here as well, aqueous dilutions of the alkali metal alkylsiliconates are employed, which can likewise be produced from highly concentrated powders (P) and (P1). Here again, by removing water from the equation in the concentrate, significant reductions can be achieved in transport and stockholding costs.

In addition to the applications already described, the powders (P) and (P1) may be used, for example, for hydrophobizing properties in the following applications: hydrophobizing of urea-formaldehyde resins; primers based on styrene acrylates; production of acrylic paints; liquids for generating an insulating layer of condensed silicate/siliconate for semiconductors; hydrophobizing of particles (e.g., peroxides, percarbonates, color pigments); stabilization of celluloses against moisture; in combination with phosphates for improving the moisture, fungus, and fire resistance of wood impregnated with them; additization of borehole rinsing fluids (e.g., alongside graphite) for reducing the loss of drilling fluid in boreholes in leached-out sand (the hydrophobic coating of particles enhances the cleaning of boreholes by preventing the rinsing fluid adhering to the particles); hydrophobizing of fire-resistant foams, panels or fire-extinguishing powders; antigraffiti coatings; additives for injectable mortars and cements; absorbers for acids and/or aqueous biological or organic media; in combination with alkali metal silicates for soil consolidation and soil hydrophobizing, as described in EP 992 565, for example; hydrophobizing additive for landfill wastes for preventing environmentally harmful leaching/extracts; acid-neutralizing and optionally reinforcing filler for elastomers; additives in combination with SiH compounds or aluminum powders for gypsum-based or cement-based foams (e.g., aerated concrete); instant mix for hydrophobic/antimicrobial treatment of textiles, plant seeds, cellulosic materials, wood, stones in combination with biocides; additive for reinforcing and hydrophobizing asphalt; catalysts based on metalasiloxanes by reaction with metal salts such as, for example, chlorides of aluminum, titanium, zinc, tungsten, lanthanum, lead, cadmium, antimony, copper, nickel, rhodium, silver, zirconium, rubidium, manganese, chromium, cobalt, vanadium, molybdenum, iron, tin, platinum, and palladium; bases which become active only on contact with water and at the same time have neutralizing and hydrophobizing effects; adjuvants to laundry detergent powders or dishwasher detergents; additive for color pigments; addition to coatings to counter scale deposits; dry hydrophobizing of all possible solids (such as fertilizers, attractants, herbicides, pesticides, pigments, hygroscopic salts, glass fibers, glass beads, natural stones, sand, chalk, slaked lime or quick lime, paper, fibers see above, biocides, concrete powders, perlite, expanded clay, expanded glass, metal powders, wood flour, wood pellets, chips, ceramic powders, terracotta powders, clay, inorganic fillers); free-flow aids; heterogeneous alkaline catalyst for raising the reactivity of organosilicon compounds in, for example, equilibration reactions; stripping additive for removing old coatings, additive for wood fiberboard panels (e.g., MDF panels).

In all of the abovementioned applications, the powders (P) and/or (P1) may also be added to an already water-containing mixture of the substrate to be hydrophobized, in solid form or optionally in dissolved form. This procedure is appropriate for example if a building material is to be blended with the powder (P) or (P1) only on the building site. The extent of the desired effect can then be adjusted easily via the amount of (P) or (P1) added.

All of the above symbols in the above formulae have their definitions in each case independently of one another. In all formulae the silicon atom is tetravalent.

In the inventive and comparative examples below, unless indicated otherwise in each case, all quantity figures and percentage figures are given by weight, and all reactions are carried out under a pressure of 0.10 MPa (abs.).

Preparation Example 1

Siliconate from methyltrimethoxysilane/KOH (1:0.85)

A 500 ml 5-neck round-bottom flask, inertized with nitrogen and fitted with paddle stirrer, dropping funnel, thermometer, and water separator with reflux condenser, is charged with 75 g (0.55 mol) of methyltrimethoxysilane (available commercially from Wacker Chemie AG) and 65 g of Isopar E (isoparaffinic hydrocarbon mixture with a boiling range of 113-143° C., available commercially from ExxonMobil). The water separator is filled to the brim with Isopar E. Accompanied by stirring at 350 rpm, a solution of 30.9 g (0.47 mol) of potassium hydroxide (85% form, available commercially from AppliChem) in 19.8 g of demineralized water is metered in over 10 minutes. In the course of this metered addition, the reaction mixture heats up to 69° C. It is brought by further heating to boiling temperature, and the stirrer speed is reduced to 50 rpm. The distillate separates off as the bottom phase in the water separator. Up to a boiling temperature of 121° C., 64.9 g of clear colorless distillate accumulate, containing—according to analysis by gas chromatography—83.3% of methanol, 14.6% of water, and 1.7% of Isopar E. The hydrolysis of the methoxy radicals in the methyltrimethoxysilane is therefore quantitative. During the distillation, a pastelike white solid separates out in the reaction mixture, and breaks down increasingly into fine particles and forms a suspension. The suspension is filtered through a Beco KD3 filter plate in a pressure suction filter, and nitrogen is passed through until the weight is constant. This gives 61.1 g of fine, white, free-flowable powder with a solids content of 100% (determined using the HR73 halogen moisture analyzer from Mettler Toledo at 160° C.). A 50% strength aqueous solution prepared with this solid exhibits no precipitation even after storage at room temperature for two weeks in the absence of air.

The thermal stability of the solid is investigated by means of differential scanning calorimetry (DSC). For a measurement, around 5 mg of substance are heated to 415° C. at a constant heating rate of 3 K/min, and the thermal fluxes which occur during this procedure are recorded. The sample holder used is a pressure-rated F20 steel crucible, which ensures that no evaporation losses are possible. In the range starting from 229° C., the substance exhibits a decomposition enthalpy of 609 J/g.

According to particle size analysis (Sympatec Helos), 100% of all the particles are smaller than 150 μm; the maximum of the distribution density is at 47 μm.

Noninventive, Comparative Example 1

Experiment in Drying an Aqueous Solution of Potassium Methylsiliconate (Silres® BS16 Wacker Chemie AG) by Baking to Remove the Water A commercially available 54% strength aqueous solution of potassium methylsiliconate (Silres® BS16, Wacker Chemie AG) is heated in a three-neck flask. The solution is concentrated by the passing of approximately 40 l/h of nitrogen 2 cm above the surface of the liquid. As the concentration increases, the product undergoes very severe foaming, and white solid gradually settles out, starting from the edge of the flask. At 122° C., the temperature rises to 277° C. over 10 minutes. The water evaporates completely during this time. White crusts adhering firmly to the edge of the flask are formed. The $^{29}$Si NMR spectrum of the solid shows the approximately quantitative loss of the methyl groups.

Preparation Example 2

Siliconate from methyltrimethoxysilane/KOH (1:0.64)

A 500 ml 5-neck round-bottom flask, inertized with nitrogen and fitted with paddle stirrer, dropping funnel, thermometer, and water separator with reflux condenser, is charged with 50 g (0.367 mol) of methyltrimethoxysilane (available commercially from Wacker Chemie AG) and 65 g of Isopar E (isoparaffinic hydrocarbon mixture with a boiling range of 113-143° C., available commercially from ExxonMobil). The water separator is filled to the brim with Isopar E. Accompanied by stirring at 300 rpm, a solution of 15.4 g (0.23 mol) of potassium hydroxide (85% form, available commercially from AppliChem) in 14.9 g (0.826 mol) of demineralized water is metered in over 12 minutes. The reaction mixture is heated to boiling temperature and the stirrer speed is reduced to 50 rpm as soon as distillation begins. The distillate separates off as the bottom phase in the water separator. Up to a boiling temperature of 85° C., 34.4 g of clear colorless distillate accumulate, containing—according to analysis by gas chromatography—87.8% of methanol, 4.9% of water, and 5.7% of Isopar E. The bottom phase is drained from the water separator, which is filled again completely with Isopar E, and water is removed in circulation up to a boiling temperature of 118° C. This produces 10.8 g of distillate as the bottom phase, containing—according to GC analysis—50.2% of methanol and 49.7% of water. The hydrolysis of the methoxy radicals in the methyltrimethoxysilane is therefore quantitative. During the distillation, a pastelike white solid separates out in the reaction mixture, and breaks down increasingly into fine particles and forms a suspension. The suspension is filtered through a Beco KD3 filter plate in a pressure suction filter, and nitrogen is passed through until the weight is constant. This gives 38 g of fine, white, free-flowable powder with a solids content of 99.7% (determined using the HR73 halogen moisture analyzer from Mettler Toledo at 160° C.). A 50% strength aqueous solution prepared with this solid exhibits no precipitation even after storage at room temperature for two weeks in the absence of air.

Only Isopar E is detectable in the gas chromatogram of the filtrate.

The elemental analysis of the solid gives 29.1% Si, 11.2% C, 3.6% H, 29.9% O, and 26.2% K, corresponding to an Si:K molar ratio of 0.65 (theoretical: 0.64).

The thermal stability of the solid is investigated by means of differential scanning calorimetry (DSC). In the range at above 213° C., the substance exhibits a decomposition enthalpy of 512 J/g.

According to particle size analysis (Sympatec Helos), 100% of all the particles are smaller than 90 μm; the maximum of the distribution density is at 23 μm.

Preparation Example 3

Siliconate from methyltrimethoxysilane/KOH (1:0.60)

A 500 ml 5-neck round-bottom flask, inertized with nitrogen and fitted with paddle stirrer, dropping funnel, thermometer, and water separator with reflux condenser, is charged with 30 g (0.22 mol) of methyltrimethoxysilane (available commercially from Wacker Chemie AG) and 50 g of Isopar E (isoparaffinic hydrocarbon mixture with a boiling range of 113-143° C., available commercially from ExxonMobil). The water separator is filled to the brim with Isopar E. Accompanied by stirring at 350 rpm, a solution of 8.7 g (0.13 mol) of potassium hydroxide (85% form, available commercially from AppliChem) in 9.1 g (0.5 mol) of demineralized water is metered in over 12 minutes. The mixture heats up to 50° C. It is heated to boiling temperature and the stirrer speed is reduced to 50 rpm as soon as distillation begins. The distillate separates off as the bottom phase in the water separator. Up to a boiling temperature of 119° C., 25.4 g of clear colorless distillate accumulate, containing—according to analysis by gas chromatography—80.4% of methanol, 18.4% of water, and 1% of Isopar E. During the distillation, a pastelike white solid separates out in the reaction mixture, and breaks down increasingly into fine particles and forms a suspension. The suspension is filtered through a Beco KD3 filter plate in a pressure suction filter, and nitrogen is passed through until the weight is constant. This gives 19.8 g of fine, white, free-flowable powder with a solids content of 100% (determined using the HR73 halogen moisture analyzer from Mettler Toledo at 160° C.). A 50% strength aqueous solution prepared with this solid exhibits no precipitation even after storage at room temperature for two weeks in the absence of air.

The thermal stability of the solid is investigated by means of differential scanning calorimetry (DSC). In the range at above 221° C., the substance exhibits a decomposition enthalpy of 468 Vg.

Preparation Example 4

200 g of a commercially available 54% strength aqueous solution of potassium methylsiliconate (Silres® BS16, Wacker Chemie AG) are heated to boiling temperature (121° C.) in a three-neck flask in a mixture with 173 g of Isopar E. 109.1 g of water separate off in the water separator. During the distillation, a pastelike white solid is separated off, which increasingly decomposes into fine particles and forms a suspension. The suspension is filtered through a Beco KD3 filter plate in a pressure suction filter, and nitrogen is passed through it to constant weight. This gives 61.1 g of fine, white, free-flowable powder with a solids content of 100% (determined using the HR73 halogen moisture analyzer from Mettler Toledo at 160° C.). A 50% strength aqueous solution prepared with this product does not exhibit any precipitates even after two-week storage at room temperature in the absence of air.

The elemental analysis of the solid gives 22.6% Si, 9.5% C, 3.3% H, 32.7% O, and 29.55% K, corresponding to a molar ratio of Si:K of 1.01.

The thermal stability of the solid is investigated by means of dynamic scanning calorimetry (DSC). Above 222° C., the substance exhibits a decomposition enthalpy of 634 J/g.

Preparation Example 5

Siliconate from methyltrimethoxysilane/propyldimethyldiethoxysilane/KOH (0.9:0.1:0.85)

A 500 ml 5-neck round-bottom flask, inertized with nitrogen and fitted with paddle stirrer, dropping funnel, thermometer, and water separator with reflux condenser, is charged with 27 g (0.198 mol) of methyltrimethoxysilane (available commercially from Wacker Chemie AG), 3.9 g (0.02) of n-propyl(methyl)diethoxysilane (prepared in the laboratory by reacting n-propyl(methyl)dichlorosilane with ethanol) and 20 g of Isopar E (isoparaffinic hydrocarbon mixture with a boiling range of 113-143° C., available commercially from ExxonMobil). The water separator is filled to the brim with Isopar E. Accompanied by stirring at 350 rpm, a solution of 12.4 g (0.188 mol) of potassium hydroxide (85% form, available commercially from AppliChem) in 7.9 g (0.44 mol) of demineralized water is metered in over 12 minutes. The mixture heats up to 48° C. It is heated to boiling temperature. The distillate separates off as the bottom phase in the water separator. Up to a boiling temperature of 95° C., 19.4 g of colorless, slightly turbid distillate accumulate, containing—according to analysis by gas chromatography—78.5% of methanol, 7.5% of ethanol, 3.5% of water, and 8.2% of Isopar E. The bottom phase is drained off from the water separator, which is made up completely with Isopar E again, and water is removed in circulation at a boiling temperature of up to 131° C. This produces 6.2 g of distillate as bottom phase, which according to GC analysis contains 46.9% of methanol, 4.7% of ethanol, and 48.4% of water. During the distillation, a pastelike white solid separates out in the reaction mixture, and breaks down increasingly into fine particles and forms a suspension. 10 g of cyclohexane are added and the suspension is filtered through a Beco KD3 filter plate in a pressure suction filter, and nitrogen is passed through to constant weight. This gives 21.4 g of fine, white, free-flowable powder with a solids content of 99.5% (determined using the HR73 halogen moisture analyzer from Mettler Toledo at 160° C.). A 50% strength aqueous solution prepared with this solid exhibits no precipitation even after storage at room temperature for two weeks in the absence of air.

Preparation Example 6

Siliconate from methyltrimethoxysilane/propyltriethoxysilane/KOH (0.75:0.25:0.85)

A 500 ml 5-neck round-bottom flask, inertized with nitrogen and fitted with paddle stirrer, dropping funnel, thermometer, and water separator with reflux condenser, is charged with 33.7 g (0.247 mol) of methyltrimethoxysilane (available commercially from Wacker Chemie AG), 17 g (0.082) of n-propyltriethoxysilane (prepared in the laboratory by reacting n-propyltrichlorosilane with ethanol) and 67.4 g of Isopar E (isoparaffinic hydrocarbon mixture with a boiling range of 113-143° C., available commercially from ExxonMobil). The water separator is filled to the brim with Isopar E. Accompanied by stirring at 250 rpm, a solution of 18.5 g (0.28 mol) of potassium hydroxide (85% form, available commercially from AppliChem) in 11.9 g (0.66 mol) of demineralized water is metered in over 12 minutes. The mixture heats up to 51° C. It is heated to boiling temperature (60° C.).

The distillate separates off as the bottom phase in the water separator. Up to a boiling temperature of 95° C., 36.1 g of colorless, slightly turbid distillate accumulate, containing— according to analysis by gas chromatography—56.7% of methanol, 25.3% of ethanol, 3.6% of water, and 11.5% of Isopar E. The bottom phase is drained off from the water separator, which is made up completely with Isopar E again, and water is removed in circulation at a boiling temperature of up to 118° C. This produces 8.2 g of distillate as bottom phase, which according to GC analysis contains 43.8% of methanol, 17.2% of ethanol, and 38.7% of water. During the distillation, a pastelike white solid separates out in the reaction mixture, and breaks down increasingly into fine particles and forms a suspension. The suspension is filtered through a Beco KD3 filter plate in a pressure suction filter, and nitrogen is passed through to constant weight. This gives 33.2 g of fine, white, free-flowable powder with a solids content of 99.5% (determined using the HR73 halogen moisture analyzer from Mettler Toledo at 160° C.). A 50% strength aqueous solution prepared with this solid exhibits no precipitation even after storage at room temperature for two weeks in the absence of air.

Preparation Example 7

Siliconate from methyltrimethoxysilane/NaOH/KOH (1.0:0.26:0.39)

A 1000 ml 4-neck glass laboratory reactor, inertized with nitrogen and fitted with jacket, paddle stirrer, dropping funnel, thermometer, and water separator with reflux condenser, is charged with 50 g (0.36 mol) of methyltrimethoxysilane (available commercially from Wacker Chemie AG) and 66.5 g of Isopar E (isoparaffinic hydrocarbon mixture with a boiling range of 113-143° C., available commercially from ExxonMobil) and heated to 40° C. via the double jacket, using heat transfer oil.

The water separator is filled to the brim with Isopar E. Accompanied by stirring at 200 rpm, a solution of 9.3 g (0.14 mol) of potassium hydroxide (85% form, available commercially from AppliChem) and 3.7 g (0.094 mol) of sodium hydroxide (98% form, available commercially from Aldrich) in 14.8 g (0.82 mol) of demineralized water is metered in over 12 minutes. The mixture heats up to 61° C. It is heated to boiling temperature (68° C.). The distillate separates off as the bottom phase in the water separator. Up to a boiling temperature of 118° C., 41.6 g of colorless, slightly turbid distillate accumulate, containing—according to analysis by gas chromatography—81.5% of methanol (=98% of theory), 16.9% of water, and 1.2% of Isopar E. During the distillation, a pastelike white solid separates out in the reaction mixture, and breaks down increasingly into fine particles and forms a suspension. The suspension is filtered through a Beco KD3 filter plate in a pressure suction filter, and nitrogen is passed through until the weight is constant. This gives 30 g of fine, white, free-flowable powder with a solids content of 99.8% (determined using the HR73 halogen moisture analyzer from Mettler Toledo at 160° C.). A 50% strength aqueous solution prepared with this solid exhibits no precipitation even after storage at room temperature for two weeks in the absence of air.

Preparation Example 8

Siliconate from methyltri-methoxysilane KOH (1.0:0.65) (drying by evaporation)

A 500 ml 5-neck glass flask, rendered inert with nitrogen and equipped with paddle stirrer, dropping funnel, thermometer, and water separator with reflux condenser, is charged with 50 g (0.36 mol) of methyl-trimethoxysilane (available commercially from Wacker Chemie AG) and 31.8 g of Isopar E (isoparaffinic hydro-carbon mixture having a boiling range of 113-143° C., available commercially from ExxonMobil). Accompanied by stirring at 300 rpm, a solution of 31.8 g of 50% strength aqueous potassium hydroxide solution (0.23 mol of potassium hydroxide) and 2.1 g (0.117 mol) of demineralized water is metered in over 10 minutes. During this metered addition, the mixture heats up to 58° C. It is heated at reflux (66° C.) for an hour and then the distillate is switched to the water separator, which is filled to the brim with Isopar E. Up to a boiling temperature of 118° C., 49 g of colorless, slightly turbid distillate are accumulated, and—according to analysis by gas chromatography—contains 84 area% of methanol, 14 area% of water, and 2 area% of Isopar E. During the distillation, a pastelike white solid separates out in the reaction mixture, and breaks down increasingly into fine particles and forms a suspension. All of the volatile constituents are distilled off with stirring at an oil bath temperature of 70° C. under 5 hPa. This gives 37.3 g of fine, white, free-flowable powder with a solids content of 99.5% (determined using the HR73 halogen moisture analyzer from Mettler Toledo at 160° C.). A 50% strength aqueous solution prepared with this powder exhibits no precipitation even after being stored at room temperature for two weeks in the absence of air. The minimum ignition energy was determined on a powder prepared analogously: up to the maximum possible ignition energy setting of 10 J, there was no ignition in the fluidized dust.

Preparation Example 9

Siliconate from methyltri-methoxysilane/trimethylmethoxysilane/KOH (0.9:0.1:0.65)

A 500 ml 5-neck round-bottom flask, rendered inert with nitrogen and equipped with paddle stirrer, dropping funnel, thermometer, and water separator with reflux condenser, is charged with 70 g (0.5 mol) of methyl-trimethoxysilane (available commercially from Wacker Chemie AG), 6 g (0.05 mol) of trimethylmethoxysilane (prepared in the laboratory by reacting trimethyl-chlorosilane with methanol), and 98.6 g of Isopar E (isoparaffinic hydrocarbon mixture having a boiling range of 113-143° C., available commercially from ExxonMobil). The water separator is filled to the brim with Isopar E. Accompanied by stirring at 300 rpm, a solution of 40.5 g of 50% strength aqueous potassium hydroxide solution (0.36 mol of potassium hydroxide) and 3.2 g of demineralized water is metered in over 6 minutes. During this metered addition, the mixture heats up to 63° C. The mixture is heated to boiling temperature (70° C.). The distillate separates out as the bottom phase in the water separator. Up to a boiling temperature of 118° C., 60.3 g of colorless, slightly turbid distillate are accumulated, and—according to analysis by gas chromatography—contains 84 area % of methanol, 10.8 area % of water, 3.3 area % of Isopar E, and 0.8 area % of trimethylmethoxysilane. The suspension which remains is subsequently evaporated to dryness with stirring under a full oil-pump vacuum (5 hPa) to 70° C. This gives 55.9 g of fine, white, free-flowable powder with a solids content of 99.9% (determined using the HR73 halogen moisture analyzer from Mettler Toledo at 160° C.). A 50% strength aqueous solution prepared with this powder exhibits no precipitation even after being stored at room temperature for two weeks in the absence of air.

Preparation Example 10

Siliconate from methyltri-methoxysilane/3,3,3-trifluoropropyltrimethoxysilane/KOH (0.9:0.1:0.65)

A 500 ml 5-neck round-bottom flask, rendered inert with nitrogen and equipped with paddle stirrer, dropping funnel, thermometer, and water separator with reflux condenser, is charged with 50 g (0.36 mol) of methyl-trimethoxysilane (available commercially from Wacker Chemie AG), 8.8 g (0.04 mol) of 3,3,3-trifluoro-propyltrimethoxysilane (available commercially from Fluka), and 39.7 g of Isopar E (isoparaffinic hydro-carbon mixture having a boiling range of 113-143° C., available commercially from ExxonMobil). The water separator is filled to the brim with Isopar E. Accompanied by stirring at 350 rpm, a solution of 17.2 g of potassium hydroxide (85% strength, available commercially from AppliChem) (0.26 mol of potassium hydroxide) and 15.3 g of demineralized water is metered in over 12 minutes. During this metered addition, the mixture heats up to 67° C. The mixture is heated to boiling temperature (70° C.). The distillate separates out as the bottom phase in the water separator. Up to a boiling temperature of 119° C., 48.5 g of colorless, slightly turbid distillate accumulate. The suspension which remains is subsequently evaporated to dryness with stirring under a full oil-pump vacuum (5 hPa) to 70° C. This gives 45.9 g of fine, white, free-flowable powder with a solids content of 99.7% (determined using the HR73 halogen moisture analyzer from Mettler Toledo at 160° C.). A 50% strength aqueous solution prepared with this powder exhibits no precipitation even after being stored at room temperature for two weeks in the absence of air.

Preparation Example 11

Siliconate from methyltri-methoxysilane/KOH (1:0.65)—Simulation of a Continuous Process a) Hydrolysis in Methanol (→aqueous, methanolic siliconate solution=solution A)

A 500 ml 5-neck round-bottom flask rendered inert with nitrogen and equipped with paddle stirrer, two dropping funnels, thermometer, and reflux condenser is charged with 25 g (0.36 mol) of methanol, which is heated to reflux (about 65° C.). Metered subsequently into the boiling methanol, in parallel and each over a period of 30 minutes, are—from one dropping funnel—71.7 g of a 36.6% strength aqueous potassium hydroxide solution (0.47 mol KOH, 2.5 mol water) and—from the other dropping funnel—100 g (0.72 mol) of methyltrimethoxy-silane (available commercially from Wacker Chemie AG). Refluxing is continued for 30 minutes, after which the amount of methanol introduced initially (25 g) is distilled off. The residue left is 165.8 g of a colorless, clear liquid (=solution A) with a solids content of 45.4% (determined using the HR73 halogen moisture analyzer from Mettler Toledo at 160° C.)

b) Hydrolysis in Hydrolyzate Solution

A 500 ml 5-neck round-bottom flask rendered inert with nitrogen and equipped with paddle stirrer, two dropping funnels, thermometer, and reflux condenser is charged with 100 g of solution A, which is heated to reflux (about 65° C.). Metered subsequently into the boiling mixture, in parallel and each over a period of 30 minutes, are—from one dropping funnel—71.7 g of a 36.6% strength aqueous potassium hydroxide solution (0.47 mol KOH, 2.5 mol water) and— from the other dropping funnel—100 g (0.72 mol) of methyltrimethoxy-silane (available commercially from Wacker Chemie AG). In the course of these metered additions, the boiling point rises to 72° C. The residue left is 267.6 g of a colorless, clear liquid (=solution B) with a solids content of 45.3% (determined using the HR73 halogen moisture analyzer from Mettler Toledo at 160° C.).

c) Powder Isolation

A 500 ml 5-neck round-bottom flask, rendered inert with nitrogen and equipped with paddle stirrer, one dropping funnel, thermometer, and water separator with reflux condenser, is charged with 100 g of Isopar E (iso-paraffinic hydrocarbon mixture having a boiling range of 113-143° C., available commercially from ExxonMobil), and this initial charge is heated to 110° C. Prior to this, the water separator was filled to the brim with Isopar E. Accompanied by stirring at 300 rpm, 262.1 g of solution B are metered in at a rate such that the temperature does not fall below 100° C. and does not exceed 110° C. The volatile constituents (principally methanol and water) present in solution B evaporate and condense in the reflux condenser. In the Isopar E, the siliconate separates out in finely divided form, to form a white suspension which is readily stirrable. 145.2 g of colorless, slightly turbid distillate are separated off as the lower phase in the water separator. The suspension which remains is subsequently evaporated to dryness with stirring under a full oil-pump vacuum (5 hPa) to 100° C. This gives 115.2 g of fine, white, free-flowable powder with a solids content of 99.8% (determined using the HR73 halogen moisture analyzer from Mettler Toledo at 160° C.). A 50% strength aqueous solution prepared with this powder does not exhibit any sedimentation even after being stored for two weeks at room temperature in the absence of air.

Application Example 1

Hydrophobizing of an Alabaster Stucco Plaster with a Potassium Methylsiliconate Powder having a Molar Alkali Metal-to-Silicon Ratio of 0.85 (Product from Preparation Example 1)

A standard commercial, pH-neutral stucco plaster in powder form (alabaster plaster from Hilliges Gipswerk GmbH and Co. KG, Osterode, Germany) was mixed effectively with varying amounts of potassium methyl-siliconate powder in dry form. This dry mix was subsequently added in portions with stirring, in accordance with a water/plaster factor of 0.6, to the mixing water, and the water and mix were stirred together using an electrically operated paddle stirrer of moderate speed, to form a homogeneous slurry. The resulting slurry was then poured into PVC rings (diameter: 80 mm, height: 20 mm) and the plaster was cured at 23° C. and 50% relative humidity over 24 hours. After the demolding of the plaster specimens from the rings, they were dried to constant weight in a forced-air drying cabinet at 40° C. For the determination of the water absorption in accordance with DIN EN 520, the specimens, following determination of the dry weight, were stored under water for 120 minutes, with the samples placed horizontally on metal grids and the water level above the highest point of the specimens being 5 mm. After 120 minutes, the specimens were taken from the water, and allowed to drip off on a water-saturated sponge, and the percentage water absorption was calculated from the wet weight and the dry weight in accordance with the following formula:

percentage water absorption={[mass(wet)−mass(dry)]/mass(dry)}·100%.

As shown in table 1, the potassium methylsiliconate powder from preparation example 1, with a molar alkali metal-to-silicon ratio of <1 (according to general formula 1), already provides very efficient hydro-phobizing of plaster. Water absorption is below 10% at a level of addition of not more than 0.6%; water absorption is less than 5% for a level of addition of not more than 0.8%. The pH of the plaster (slurry) is increased by the metered addition of the potassium methylsiliconate powder: it was 7 with no addition, 9 on addition of 0.2% of potassium methylsiliconate powder, and 10 on addition of 0.6% of potassium methyl-siliconate powder (measured using indicator sticks).

In the further application examples 2-5, typical commercial plasters in powder form (Goldband light finishing plaster and machine-application plaster MP 75 from Knauf Gips KG, Iphofen, Germany) were mixed effectively with varying amounts of potassium methyl-siliconate powder in dry form. This dry mix was then added in portions and with stirring to the mixing water, in accordance with the recipe indicated on the pack, and the water and mix were stirred together using an electrically operated paddle stirrer at moderate speed, to form a homogeneous slurry (Goldband light finishing plaster: 300 g plaster powder and 200 g water; machine-application plaster MP 75: 300 g plaster powder and 180 g water —in each case as per pack instructions). The resulting slurry was then poured into PVC rings (diameter: 80 mm, height: 20 mm). Drying, demolding, and determination of the percentage water absorption took place as described above for application example 1.

Application Example 2

Hydrophobizing of Two Plasters with a Potassium Methylsiliconate Powder having a Molar Alkali Metal-to-Silicon Ratio of 0.85 (Product from Preparation Example 1)

Table 1 shows that a potassium methylsiliconate powder with a molar alkali metal-to-silicon ratio of 1 (as per formula 1) likewise provides very efficient hydro-phobizing of plasters. Depending on the plaster used, the water absorption is less than 10% at a level of addition of not more than 0.3%, and is not more than 5% at a level of addition of not more than 0.4%.

Application Example 3

Hydrophobizing of Two Plasters with a Potassium Methylsiliconate Powder having a Molar Alkali Metal-to-Silicon ratio of 0.64 (Product from Preparation Example 2)

As a result of the reduction in alkali metal content to a molar alkali metal-to-silicon ratio of 0.64, the efficiency of the hydrophobizing agent can be increased further. In this example, water absorption is below 10% for one plaster even at a level of addition of not more than 0.2%; water absorption is less than 5% for both plasters even at a level of addition of not more than 0.3%. The pH of the plasters (slurry) is unaffected by the metered addition of the potassium methylsiliconate powder: it was 12.5 with no addition, 12.5 on addition of 1.0% of potassium methylsiliconate powder (measured using indicator sticks).

Application Example 4

If the water absorption test is carried out not, as in application example 3, immediately after the drying of the specimens, but instead only after three days, and if the rest time is extended, then it is possible again to observe an increase in the efficiency of the hydro-phobizing agent. At a level of addition of 0.2%, both plasters now absorb only not quite 5% of water; water absorption is significantly below 5% at a level of addition of not more than 0.3%, for both plasters.

Application Example 5

A comparison with the dry-mix hydrophobizing additive SILRES® PULVER G (Wacker Chemie AG) emphasizes the difference relative to products currently customary commercially. 10% capillary water absorption is achieved only by adding 1.4% of SILRES® PULVER G; capillary water absorption is below 5% by means of 1.6% of SILRES® PULVER G.

TABLE 1

Water absorption of plaster specimens in accordance with DIN EN 520

| Level of addition (% by wt. based on plaster solids content) | 1 Alabaster plaster | 2 Knauf MP 75 | 2 Knauf Goldband | 3 Knauf MP 75 | 3 Knauf Goldband | 4 Knauf MP 75 | 4 Knauf Goldband | 5* Knauf Goldband |
|---|---|---|---|---|---|---|---|---|
| 0 | 35.8 | 39.9 | 36.3 | 39.9 | 36.3 | 39.9 | 36.3 | 36.3 |
| 0.2 | | 10.2 | 31.5 | 8.4 | 25.3 | 5.9 | 6.8 | 36.0 |
| 0.3 | | 4.0 | 21.8 | 3.4 | 4.3 | 2.7 | 1.1 | |
| 0.4 | | 3.4 | 2.3 | 2.4 | 1.4 | 2.4 | 1.2 | 29.0 |
| 0.5 | | 2.2 | 1.4 | 2.1 | 1.1 | 2.1 | 1.0 | |
| 0.6 | 8.0 | 2.0 | 1.1 | 2.1 | 1.0 | 2.3 | 1.1 | 24.0 |
| 0.8 | 4.6 | 1.8 | 0.9 | 2.5 | 0.8 | 2.4 | 0.9 | 13.1 |
| 1.0 | 2.1 | 1.6 | 0.8 | 1.7 | 0.9 | 2.0 | 1.1 | 12.0 |
| 1.2 | | 1.5 | 0.7 | | | | | 13.2 |
| 1.3 | 0.6 | | | | | | | |
| 1.4 | | | | | | | | 10.7 |
| 1.5 | 0.7 | | | | | | | |
| 1.6 | | | | | | | | 3.2 |
| 1.8 | | | | | | | | 1.6 |

*not inventive

Application Example 6

Customary commercial red bricks from a Spanish manufacturer were given a water-repellent impregnation by immersion into aqueous potassium methylsiliconate solutions. Here, the effect of a solution of inventive potassium methylsiliconate powder (molar potassium-to-silicon ratio of 0.85; product from preparation example 1) in water was compared with an aqueous dilution of SILRES® BS 16 (potassium methylsiliconate, 54% strength in water). The bricks were immersed fully into the solutions for 30 seconds. The bricks were then stored for 7 days at 23° C. and 50% relative humidity, after which they were dried to constant weight in a forced-air drying cabinet at 40° C. The water absorption was tested by water storage over 24 hours in accordance with DIN EN 15148 (average value formed from duplicate determination).

Likewise determined were the depth of penetration of the impregnation, by breaking of the bricks and application of trickle water (average value on all sides formed from duplicate determination).

TABLE 2

Water absorption over 24 hours in accordance with DIN EN 15148:

| Impregnating composition | Proportion | Averaged water absorption (24 h) (% by wt.) | Averaged depth of penetration (mm) |
|---|---|---|---|
| SILRES ® BS 16* | 1 part by wt. BS 16 70 parts by wt. water | 1.2 | 5 |
| Potassium methyl-siliconate powder (K:Si = 0.85) | 0.5 part powder 70 parts by wt. water | 1.1 | 5 |
| Without* impregnation | — | 13.9 | 0 |

*not inventive

Application Example 7

One part of SILRES® BS 16 from Wacker Chemie AG is mixed with 70 parts of water (parts by weight) to give a clear solution. Products made from fired clay, such as roof shingles, bricks, clinker bricks, flowerpots or paving slabs, for example, are immersed in this solution or sprayed with the solution. The same clear solution with the same molar content of active organosilicon compound is obtained by dissolving 0.5 part of potassium methylsiliconate powder from preparation example 1 (molar potassium-to-silicon ratio of 0.85) in 70 parts of water (parts by weight). Even after 10 days, the solution was clear and ready for application.

Comparative Example 1

A sodium methylsiliconate powder prepared in accordance with example 1 of U.S. Pat. No. 2,438,055 was compared with a sodium methylsiliconate powder of the same stoichiometry but prepared by the process of the invention.

TABLE 3

Water absorption of plaster specimens in accordance with DIN EN 520

| | | Level of addition (% by wt. based on plaster solids content) | |
|---|---|---|---|
| Process of U.S. Pat. No. 2,438,055* | Plaster Knauf MP 75 | 0.10 21.7 | 0.30 |
| | Knauf Goldband | | 6.3 |
| Inventive | Knauf MP 75 | 12.6 | |
| | Knauf Goldband | | 1.8 |

*not inventive

Comparative Example 2

A sodium methylsiliconate powder prepared in accordance with example 1 of U.S. Pat. No. 2,803,561 was compared with a sodium methylsiliconate powder of the same stoichiometry but prepared by the process of the invention.

TABLE 4

Water absorption of plaster specimens in accordance with DIN EN 520

| | | Level of addition (% by wt. based on plaster solids content) | |
|---|---|---|---|
| Process of U.S. Pat. No. 2,803,561* | Plaster Knauf MP 75 | 0.15 8.0 | 0.30 |
| | Knauf Goldband | | 7.6 |
| Inventive | Knauf MP 75 | 3.2 | |
| | Knauf Goldband | | 1.8 |

*not inventive

Comparative Example 3

A sodium methylsiliconate powder prepared in accordance with example 1 of DE 1176137 was compared with a sodium methylsiliconate powder of the same stoichiometry but prepared by the process of the invention.

TABLE 5

Water absorption of plaster specimens in accordance with DIN EN 520

| | | Level of addition (% by wt. based on plaster solids content) | |
|---|---|---|---|
| Process of DE 1176137* | Plaster Knauf MP 75 | 0.15 25.3 | 0.40 |
| | Knauf Goldband | | 2.3 |
| Inventive | Knauf MP 75 | 3.2 | |
| | Knauf Goldband | | 1.4 |

*not inventive

Application Example 8

Hydrophobizing of a Stucco Plaster with a Mixture of a Methylhydrogenpolysiloxane (SILRES® BS 94 from Wacker Chemie AG) and a Potassium Methylsiliconate Powder with a Molar Alkali Metal-to-Silicon Ratio of 0.64 (Product from Preparation Example 2)

In a similar way as for application example 1, a pH-neutral conveyor-line stucco plaster in powder form (Knauf Gips KG, Iphofen, Germany) was first mixed effectively with a defined amount of potassium methyl-siliconate powder from preparation example 2 in dry form. Separately, the mixing water was admixed with the defined amount of SILRES® BS 94 and homogenized using a homogenizer (Ultraturrax) at around 10,000 rpm for 20 seconds. The dry mix was then added, in portions and with stirring, to the mixing water, in accordance with a water/plaster factor of 0.60, and the water and mix were stirred together, using an electrically operated paddle stirrer of moderate speed, to give a homogeneous plaster slurry. The specimens were produced and treated in a similar way as for application example 1, and the water absorption was also determined along the lines of application example 1. As is shown in table 8, the combination of SIL-RES® BS 94 and potassium methyl-siliconate powder from preparation example 2 brings about a significantly more efficient hydrophobizing than the use of the respective individual component. Where, for example, one quarter of the methyl-hydrogen-polysiloxane is replaced in 8/4 by siliconate powder (8/7), the water absorption is reduced by more than 50%. In the case of the mixtures (8/2 and 8/3) with a 0.2% by weight fraction of each of the individual component (SILRES® BS94 or potassium methylsiliconate powder from preparation example 2), the addition of 0.1% by weight of the respective other individual component leads to water absorption figures of below 5% (8/5 and 8/6).

TABLE 6

Water absorption of plaster specimens in accordance with DIN EN 520

| Ex. | Level of addition (% by wt. based on plaster solids content) | | Water absorption in % by wt. (2 h) |
|---|---|---|---|
| | SILRES® BS 94 | K methylsiliconate powder from prep. ex. 2 | |
| 8/1 | 0 | 0 | 37.4 |
| 8/2 | 0 | 0.2 | 16.8 |
| 8/3 | 0.2 | 0 | 6.4 |
| 8/4 | 0.4 | 0 | 6.3 |
| 8/5 | 0.1 | 0.2 | 3.7 |
| 8/6 | 0.2 | 0.1 | 2.9 |
| 8/7 | 0.3 | 0.1 | 2.7 |

Application Example 9

Hydrophobizing of Soil Samples

This example shows that the siliconates of the invention, in combination with sodium silicates, produce highly efficient soil hydrophobizing agents, which in terms of their activity at least match the aqueous solution available commercially. The activity is present even when the mixture does not dissolve completely in water.

The test substrate used was earth with a bulk density of 1.5983 g/cm$^3$ and a moisture content of 3.65% (determined after storage at 110° C. for 24 hours). In each case 500 g of earth were admixed in a paddle mixer with the respective additive and with an amount of water such as to result in a moisture content of 4% by weight. Stirring was continued for 5 minutes, the mixture was introduced into a hydraulic press, and it was compressed within 5 seconds under 300 bar to form a block with dimensions of 12.5×6×3.5 cm. The specimens thus produced were stored at room temperature for 7 days prior to testing.

Testing:

The blocks were stood on their smallest surface in Petri dishes. To investigate the resistance to capillary water absorption, the Petri dishes were filled with water to a height of 1 cm. The water level was maintained constant during the test duration.

The following additives were employed:

WACKER SILRES® 501 dry soil=commercially available aqueous solution of 45% by weight WACKER SILRES® BS 16 (=54% strength aqueous solution of potassium methyl-siliconate) and 23% by weight Woellner sodium silicate 38/40 (=36% strength aqueous solution of sodium silicate, available from Woellner GmbH & Co. KG), and also mixtures of 75% by weight potassium methylsiliconate powder from preparation example 2 (K:Si=0.64) with in each case 25% by weight of solid sodium silicates from Woellner GmbH & Co. KG:

Simet AP (=mixture AP), Simet AG (=mixture AG), and Sikalon A (=mixture A)

TABLE 7

| | Level of addition (based on 500 g of earth) | | |
|---|---|---|---|
| Ex. | Additive | Water | Result |
| 9/1 | 0 | 1.75 g | <10 sec stable |
| 9/2 | 1.55 (SILRES ® 501)*) (=0.52 g solids) | 0.71 g | >4 weeks stable |
| 9/3 | 0.52 g mixture AP*) | 1.75 g | >4 weeks stable |
| 9/4 | 0.52 g mixture A**) | 1.75 g | >4 weeks stable |
| 9/5 | 0.52 g mixture AG**) | 1.75 g | >4 weeks stable |

*)infinitely miscible with water
**)not fully water-soluble

The invention claimed is:

1. A powder comprising at least one particulate salt of at least one organosilanol, of a hydrolysis/condensation product thereof, or of at least one organosilanol together with the hydrolysis/condensation products thereof, wherein cations of the at least one salt are selected from the group consisting of alkali metal ions, ammonium ions, organoammonium ions and mixtures thereof, wherein the molar ratio of cation to silicon is from 0.1 to 0.89.

2. A process for producing an organosilanolate powder of claim 1, comprising, in a first step, hydrolyzing organosilane(s) of the formula 1

$$(R^1)_a Si(Y)_b (—Si(R^2)_{3-c}(Y)_c)_d \quad (1)$$

or their hydrolysis/condensation products, or a mixture thereof, where $R^1$ and $R^2$ are each independently a monovalent, Si—C-bonded $C_{1-30}$ hydrocarbon radical which is unsubstituted or is substituted by halogen atoms, amino groups or $C_{1-6}$ alkyl- or $C_{1-6}$ alkoxy-substituted silyl groups, in which one or more nonadjacent —$CH_2$— units in the hydrocarbon radical are optionally replaced by groups —O—, —S—, or —$NR^3$—, and in which one or more nonadjacent =CH— units may be replaced by —N=, $R^3$ is hydrogen or a monovalent $C_{1-8}$ hydrocarbon radical which is unsubstituted or substituted by halogen atoms or $NH_2$ groups, Y is hydrogen, F, Cl, Br, or $OR^4$, $R^4$ is a monovalent $C_{1-10}$ hydrocarbon radical which is unsubstituted or substituted by halogen atoms or silyl groups, in which one or more nonadjacent $CH_2$ units are optionally replaced by groups —O—, —S—, or —$NR^3$—, and in which one or more nonadjacent =CH— units may be replaced by —N=, a is 1, 2 or 3, and b, c, and d are 0, 1, 2 or 3, with the provisos that b+c≥1 and a+b+d=4, hydrolyzing takes place in the presence of water and at least one basic salt of a cation selected from the group consisting of alkali metal ions, ammonium ions, and organoammonium ions, the amount of basic salt being calculated such that per mole of silicon there is at least 0.1 mol and not more than 0.89 mol of cations, and, if the organosilanes of the general formula 1 contain radicals selected from F, Cl, and Br, a further mole of basic salt is present per mole of F, Cl, and Br, and at least 50% of the radicals $R^1$ and $R^2$ contain not more than 3 C atoms;

in a second step, removing a liberated compound HY from the reaction mixture during or after hydrolyzing, in the form of vapor and/or gas, and in the presence of an inert liquid F which is inert under the reaction conditions, which has a boiling point above that of the compound HY, and has a solvency of not more than 1% by weight for the siliconate salt in solid form, at 100° C./1 bar, in a third step, removing water by distillation to form a suspension of the siliconate salt in the inert liquid F, and in a fourth step, isolating the siliconate salt in the form of a powder by filtration, centrifugation, sedimentation or by evaporation of the inert liquid F.

3. The process of claim 2, in which the first step is carried out in the absence of the inert liquid F, and in simultaneously implemented second and third steps, the siliconate salt solution thus formed is contacted with the inert liquid F under conditions in which the volatile constituents of the solution evaporate and the siliconate salt is precipitated in the form of a solid.

4. The process of claim 2, in which the basic salts are selected from sodium hydroxide and potassium hydroxide.

5. The process of claim 3, in which the basic salts are selected from sodium hydroxide and potassium hydroxide.

6. The process of claim 2, in which hydrocarbons are used as inert liquid F.

7. An organosilanolate powder produced by the process of claim 2.

8. The powder of claim 1, which has a water solubility of at least 20% by weight at 20° C.

9. The powder of claim, 7 which has a water solubility of at least 20% by weight at 20° C.

10. The powder of claim 1, which has an average particle size of not more than 500 μm.

11. The powder of claim 7, which has an average particle size of not more than 500 μm.

12. The process of claim 2 where $R^1$ and $R^2$ are each independently an alkyl radical having 1 to 6 carbon atoms.

13. The process of claim 7 where $R^1$ and $R^2$ are each independently an alkyl radical having 1 to 6 carbon atoms.

14. The process of claim 2, where Y is $OR^4$ and $R^4$ is an alkyl radical having 1 to 4 carbon atoms.

15. The process of claim 7, where Y is $OR^4$ and $R^4$ is an alkyl radical having 1 to 4 carbon atoms.

16. A process of hydrophobing a substrate, comprising applying an organosilanolate powder of claim 1 to the substrate, or incorporating into the substrate an organosilanolate powder of claim 1.

17. The process of claim 16, wherein the substrate comprises a mineral building material.

18. A process of hydrophobing a substrate, comprising applying an organosilanolate powder of claim 7 to the substrate, or incorporating into the substrate an organosilonolate powder of claim 7.

19. The process of claim 18, where the substrate comprises a mineral building material.

20. The process of claim 19, where the mineral building material comprises gypsum.

21. A building material in powder form, comprising gypsum, and further comprising 0.01% to 10% of an organosilanolate-containing powder of claim 7.

22. The powder of claim 1, further comprising gypsum, and having a content from 0.01 to 10.0 weight percent based on the total weight of the powder of at least one particulate salt of at least one organosilanol, of a hydrolysis/condensation product thereof, or of at least one organosilanol together with the hydrolysis/condensation products thereof, wherein cations of the at least one salt are selected from the group consisting of alkali metal ions, ammonium ions, organoammonium ions and mixtures thereof, wherein the molar ratio of cation to silicon is from 0.1 to 0.89.

* * * * *